Dec. 28, 1948. J. F. STYER Plant Pat. 817
JAPANESE HOLLY PLANT
Filed Aug. 28, 1946
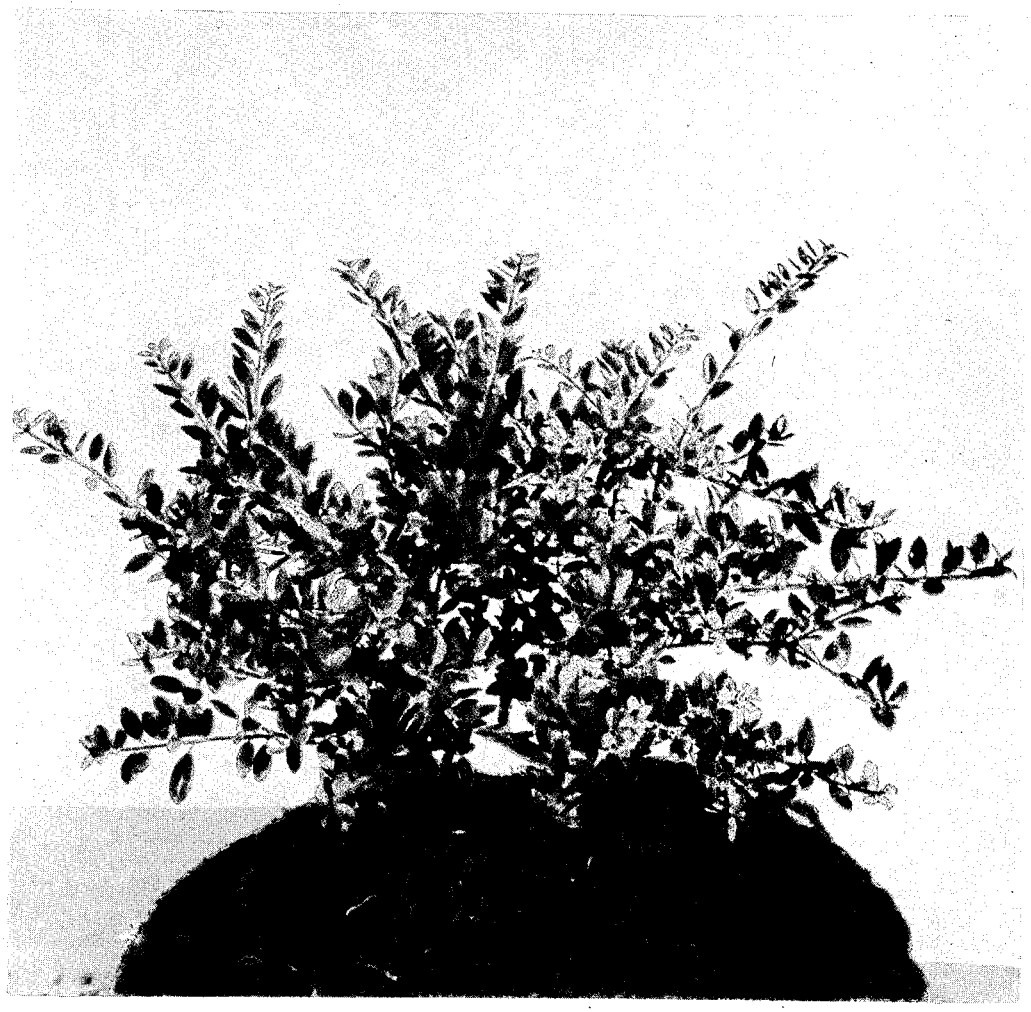
Inventor
John Franklin Styer
By
Frederick Schafer
Attorney Patented Dec. 28, 1948

Plant Pat. 817

UNITED STATES PATENT OFFICE

817

JAPANESE HOLLY PLANT

John Franklin Styer, Concordville, Pa.

Application August 28, 1946, Serial No. 693,426

1 Claim. (Cl. 47—59)

The present invention relates to a new variety of holly plant and more particularly to a new and distinct variety of Japanese holly, *Ilex crenata*.

The present holly originated from seed in the nursery of the discoverer at Concordville, Pennsylvania, being one of a large number of seedlings. The new plant was selected from these for its striking variation from the type and propagated by asexual means, that is from cuttings. The young plants thus asexually reproduced exhibit identical characteristics to the original plant and to each other, which would not be true if propagated by other than asexual means.

Heretofore, Japanese holly required clipping or shearing to maintain a low form, which occupied time and added to the cost to the consumer. Furthermore, such plants failed to maintain their clipped form and therefore were unpopular.

The holly forming the subject matter of this invention is characterized particularly by virtually all growth tending to the horizontal, producing a fast growing, low spreading plant, which retains the described form without clipping or shearing. Further novel characteristics reside in smallness of leaves, hardiness, substantially horizontal branch growth associated with free branching in all directions, and plant form more broad than tall.

The new variety of Japanese holly is well-formed, attractive and suitable for use as an evergreen shrub, for specimens, masses or hedges in landscape gardening. Its rapid and substantially horizontal growth makes it particularly adapted for planting against foundations of homes, buildings, or low walls, or in the foreground of any kind of mass planting where much height is undesirable. It is useful in preference to all other low and spreading evergreen plants in that its evergreen color which is light green does not undergo variations with the seasons but is virtually changeless. It is useful in preference to most other low and spreading evergreen plants in that it is free from serious insect or pest or disease attack. It is further useful in preference to most other low and spreading evergreen plants in that it is tolerant of extreme wetness or dryness, and to a large degree of shade.

The drawing shows in natural colors the new and distinct variety of Japanese holly.

As a convenient summary the following detailed description is given:

Plant form: Much-branched woody evergreen shrub, growing to about six feet in height, low spreading, more broad than tall, branching freely in all directions, substantially all branch growth becoming horizontal.

Growth character: Normal for the new variety, four to eight inches per year, evergreen, hardy to Boston, Albany, and northern Ohio.

Leaves: Alternate; petioled; oval or obovate, crenately serrate, glabrous, ½ to ⅞ inches long by ¼ to ½ inch broad; evergreen; not arranged in ranks.

Flowers: Staminate; calyx-lobes, petals and stamens, 4; inconspicuous, usually solitary, white, borne in May or June on present year's growth.

Berries: None.

Comparison: In the following comparison with *Ilex crenata* Helleri, characteristic differences possessed by the present Japanese holly plant will be pointed out. *Ilex crenata* Helleri is of such extreme slowness of growth that it is extremely dense and dwarf, resulting in a compact plant. In the climate in the vicinity of Philadelphia, it makes 1 to 2 inches of growth per year. This results in profuse and very close branching. In contrast to this, the Japanese holly plant which is the subject of this application makes 4 to 8 inches of growth per year. Hence it is more open in character. In the vicinity of Philadelphia, *Ilex crenata* Helleri kills back in winter about as much as it grows in summer. On the other hand, the Japanese holly plant which is the subject of this application makes satisfactory growth. This difference in growth is important and is so great that the present Japanese holly plant is commercially useful throughout the year. A further difference is that the leaves of *Ilex crenata* Helleri average one-third to one-half smaller than the leaves of the present Japanese holly plant.

I claim:

The new variety of *Ilex crenata*, Japanese holly plant, characterized particularly by branch growth substantially horizontal, associated with rapid growth and free branching in all directions, with leaves smaller than the ordinary or type of the species, with great plant hardiness and with plant form more broad than tall, as shown and described.

JOHN FRANKLIN STYER.

REFERENCES CITED

The following references are of record in the file of this patent:

Am. Nurseryman, vol. 79, p. 21, "*Ilex Crenata* Helleri," January 1, 1944.